US009410933B2

(12) United States Patent
Tam

(10) Patent No.: US 9,410,933 B2
(45) Date of Patent: Aug. 9, 2016

(54) METHOD AND APPARATUS FOR DETERMINING THE SALINITY OF A SAMPLE

(71) Applicant: Daniel W. S. Tam, San Diego, CA (US)

(72) Inventor: Daniel W. S. Tam, San Diego, CA (US)

(73) Assignee: The United States of America a represented by the Secretary of Navy, Washington, DC (US)

( * ) Notice: Subject to any disclaimer, the term of this patent is extended or adjusted under 35 U.S.C. 154(b) by 218 days.

(21) Appl. No.: 14/290,497

(22) Filed: May 29, 2014

(65) Prior Publication Data

US 2015/0346124 A1 Dec. 3, 2015

(51) Int. Cl.
*G01N 33/24* (2006.01)
*G01N 27/02* (2006.01)

(52) U.S. Cl.
CPC ............... *G01N 33/24* (2013.01); *G01N 27/02* (2013.01); *G01N 27/023* (2013.01)

(58) Field of Classification Search
CPC ................................ G01N 27/02; G01N 33/24
See application file for complete search history.

(56) References Cited

U.S. PATENT DOCUMENTS

| 3,404,335 A | 10/1968 | Kidder |
| 3,404,336 A | 10/1968 | Rosenthal |
| 5,680,051 A | 10/1997 | Wakamatsu |
| 8,525,527 B2 * | 9/2013 | Skaling .................. G01N 27/00 324/642 |
| 9,000,776 B1 * | 4/2015 | Tam ..................... G06F 17/5036 324/324 |
| 2001/0011155 A1 | 8/2001 | Rapoport |
| 2004/0085077 A1 * | 5/2004 | Nyfors .................... G01N 22/00 324/637 |
| 2007/0252578 A1 * | 11/2007 | Luo ..................... G01R 1/06788 324/126 |
| 2008/0224922 A1 * | 9/2008 | Cleland .................. B82Y 35/00 342/175 |
| 2009/0129982 A1 * | 5/2009 | Rapoport ............... G01N 27/08 422/82.01 |

OTHER PUBLICATIONS

Honeywell; 5000TC Toroidal Conductivity Sensor; Product information webpage; available online at https://www.honeywellprocess.com/en-US/explore/products/instrumentation/analytical-instruments-and-sensors/default/Pages/5000-tc-toroidal-conductivity-sensor.aspx; accessed on Apr. 24, 2014.
Agilent; Impedance and Network Analysis Application List; Product Information Guide; available online; published Oct. 2012.
Emerson; Theory and Application of Conductivity; available online at http://www.raihome.com; 2010.
Gadani et al.; Effect of Salinity on the Dielectric Properties of Water; Indian Journal of Pure & Applied Physics, vol. 50, pp. 405-410; Jun. 2012.

(Continued)

*Primary Examiner* — Jeff Natalini
(74) *Attorney, Agent, or Firm* — SPAWAR Systems Center Pacific; Kyle Eppele; J. Eric Anderson

(57) ABSTRACT

An apparatus for determining the salinity of an ionic sample consisting essentially of: a single current probe having a central aperture large enough to accommodate a tube that contains the ionic sample; a network analyzer electrically coupled to the current probe, wherein the network analyzer is configured to transmit power into the ionic sample when the tube containing the ionic sample is positioned within the central aperture and then further configured to measure the return loss parameter of a signal voltage waveform reflected from the ionic solution; and a reference table of reference sample properties to which the measured return loss parameter may be compared to determine the level of salinity of the ionic sample.

20 Claims, 13 Drawing Sheets

(56) References Cited

OTHER PUBLICATIONS

Lasne Y. et al.; Effect of Salinity on the Dielectric Properties of Geological Materials : Implication for Soil Moisture Detection by Means of Remote Sensing; IEEE publication; 2007.

Rayoriya K. R. S. et al.; Tunable Liquid Dielectric Antenna; International Journal of Engineering and Technology; 2012.

Onderzoek et al.; Salinity Sensors; Vlaams Instituut Voor De Zee; available online at http://www.vliz.be/wiki/Salinity_sensors; Sep. 2013.

Emerson 2; Installation & Calibration Equipment, Sensor & Instrument Mounting, Accessories, Systems and More; Rosemont Analytical; available online; 2012.

* cited by examiner

| Excel Correlation Analysis | UHF2 | UHF2+t ube | UHF2+t ube+RO | UHF2+t ube+tap | UHF2+t ube+dr inking | UHF2+ tube+0 .125TS P Salt | UHF2+ tube+0 .25TSP Salt | UHF2+ tube+0 .5TSP Salt | UHF2+t ube+1T SP Salt | UHF2+t ube+2T SP Salt | UHF2+t ube+3T SP Salt | UHF2+t ube+4T SP Salt | UHF2+t ube+5T SP Salt | UHF2+t ube+6T SP Salt | UHF2+tu be+brine | UHF2+t ube+IB Ocean | UHF2+ tube+ Urine 1 | UHF2+ tube+ Urine 2 |
|---|---|---|---|---|---|---|---|---|---|---|---|---|---|---|---|---|---|---|
| UHF2 | 1.000 | | | | | | | | | | | | | | | | | |
| UHF2+tube | 0.995 | 1.000 | | | | | | | | | | | | | | | | |
| UHF2+tube+RO | 0.312 | 0.323 | 1.000 | | | | | | | | | | | | | | | |
| UHF2+tube+tap | 0.319 | 0.330 | 0.999 | 1.000 | | | | | | | | | | | | | | |
| UHF2+tube+drinking | 0.295 | 0.305 | 0.998 | 0.998 | 1.000 | | | | | | | | | | | | | |
| UHF2 + tube+0.125TSP Salt | 0.263 | 0.274 | 0.994 | 0.993 | 0.997 | 1.000 | | | | | | | | | | | | |
| UHF2+tube+0.25TSP Salt | 0.270 | 0.280 | 0.992 | 0.992 | 0.995 | 0.999 | 1.000 | | | | | | | | | | | |
| UHF2+tube+0.5TSP Salt | 0.254 | 0.264 | 0.983 | 0.982 | 0.987 | 0.996 | 0.997 | 1.000 | | | | | | | | | | |
| UHF2+tube+1TSP Salt | 0.270 | 0.280 | 0.956 | 0.951 | 0.962 | 0.974 | 0.974 | 0.986 | 1.000 | | | | | | | | | |
| UHF2+tube+2TSP Salt | 0.226 | 0.234 | 0.924 | 0.917 | 0.934 | 0.949 | 0.948 | 0.965 | 0.991 | 1.000 | | | | | | | | |
| UHF2+tube+3TSP Salt | 0.229 | 0.236 | 0.909 | 0.902 | 0.921 | 0.936 | 0.934 | 0.951 | 0.980 | 0.997 | 1.000 | | | | | | | |
| UHF2+tube+4TSP Salt | 0.234 | 0.242 | 0.907 | 0.900 | 0.920 | 0.934 | 0.931 | 0.947 | 0.975 | 0.993 | 0.999 | 1.000 | | | | | | |
| UHF2+tube+5TSP Salt | 0.237 | 0.244 | 0.913 | 0.907 | 0.926 | 0.939 | 0.935 | 0.949 | 0.974 | 0.991 | 0.998 | 0.999 | 1.000 | | | | | |
| UHF2+tube+6TSP Salt | 0.239 | 0.246 | 0.915 | 0.909 | 0.928 | 0.940 | 0.936 | 0.949 | 0.972 | 0.990 | 0.997 | 0.999 | 1.000 | 1.000 | | | | |
| UHF2+tube+brine | 0.231 | 0.237 | 0.930 | 0.926 | 0.943 | 0.946 | 0.939 | 0.939 | 0.939 | 0.949 | 0.958 | 0.965 | 0.973 | 0.976 | 1.000 | | | |
| UHF2+tube+IB Ocean | 0.228 | 0.235 | 0.897 | 0.891 | 0.911 | 0.925 | 0.922 | 0.937 | 0.963 | 0.985 | 0.995 | 0.998 | 0.999 | 0.999 | 0.970 | 1.000 | | |
| UHF2+tube+Urine 1 | 0.215 | 0.223 | 0.934 | 0.928 | 0.945 | 0.961 | 0.961 | 0.976 | 0.994 | 0.997 | 0.991 | 0.987 | 0.986 | 0.985 | 0.953 | 0.980 | 1.000 | |
| UHF2+tube+Urine 2 | 0.255 | 0.264 | 0.950 | 0.944 | 0.957 | 0.969 | 0.970 | 0.983 | 1.000 | 0.994 | 0.983 | 0.977 | 0.976 | 0.974 | 0.938 | 0.956 | 0.995 | 1.000 |

Fig. 13

METHOD AND APPARATUS FOR DETERMINING THE SALINITY OF A SAMPLE

FEDERALLY-SPONSORED RESEARCH AND DEVELOPMENT

The United States Government has ownership rights in this invention. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 102025.

BACKGROUND OF THE INVENTION

Previous methods for measuring the salinity of an aqueous solution involved immersing voltage probe electrodes (i.e., two inductive coils or two ring transformers using toroids that were separated from each other by a fixed distance) in the aqueous solution. In the previous methods, an alternating current (I) is applied to the two measurement electrodes or coils to determine the voltage (V) and resulting resistance (R) using Ohm's law and the conductance is defined to be 1/R. The salinity of the aqueous solution was then determined from the conductance. A new method is needed to determine the salinity of a substance.

SUMMARY

Disclosed herein is a method and apparatus for determining the salinity of an ionic sample. The apparatus consists essentially of the following elements: a single current probe, a network analyzer, and a reference table of reference sample properties. The single current probe has a central aperture large enough to accommodate a tube that contains the ionic sample. The network analyzer is electrically coupled to the current probe and is configured to transmit power into the ionic sample when the tube containing the ionic sample is positioned within the central aperture. The network analyzer is also configured to measure a return loss parameter of a signal voltage waveform reflected from the ionic solution. The reference table is used to determine the level of salinity of the ionic sample by finding the reference sample whose properties most closely match the measured return loss parameter.

The method for determining the salinity of a sample may be described as comprising the following eight steps. The first step provides for providing a toroidal current probe having a central aperture. The second step provides for positioning a tube within the central aperture such that the tube extends through and substantially fills the central aperture. The third step provides for electrically coupling the current probe to a network analyzer with a radio frequency (RF) cable. The fourth step provides for measuring with the network analyzer the return loss of the combination of the RF cable, the current probe, and the tube when nothing but air occupies the tube. The fifth step provides for filling the tube in turn with reference samples having known salt concentrations, and measuring with the network analyzer the return loss for each reference sample. The sixth step provides for populating a reference table of return loss values with the measured return losses from the fourth and fifth steps. The seventh step provides for filling the tube with a test sample having an unknown salinity and measuring the return loss of the test sample. The eighth step provides for comparing the measured return loss of the test sample with the return loss values in the reference table to find the closest match and assigning the corresponding salinity concentration of the closest match to the test sample.

Alternatively, the method for determining the salinity of a sample may be described as comprising the following eight steps. The first step provides for providing a toroidal current probe having a central aperture. The second step provides for positioning a non-conductive tube within the central aperture such that the tube extends through and substantially fills the central aperture. The third step provides for electrically coupling the current probe to a network analyzer with a radio frequency (RF) cable. The fourth step provides for measuring with the network analyzer the return loss of the combination of the RF cable, the current probe, and the tube when nothing but air occupies the tube to calibrate the network analyzer. The fifth step provides for populating a reference table with resonance frequency, bandwidth, and amplitude properties for a plurality of reference aqueous solutions. The sixth step provides for filling the tube with an aqueous solution test sample having an unknown salinity and measuring the return loss of the test sample. The seventh step provides for obtaining resonance frequency, bandwidth, and amplitude properties of the test sample based on the measured return loss. The eighth step provides for comparing the properties of the test sample with the properties in the reference table to find the closest match aqueous solution and assigning a corresponding salinity concentration of the closest match aqueous solution to the test sample.

BRIEF DESCRIPTION OF THE DRAWINGS

Throughout the several views, like elements are referenced using like references. The elements in the figures are not drawn to scale and some dimensions are exaggerated for clarity.

FIG. 13 is a table showing the results of a correlation analysis.

DETAILED DESCRIPTION OF EMBODIMENTS

Figure 1:
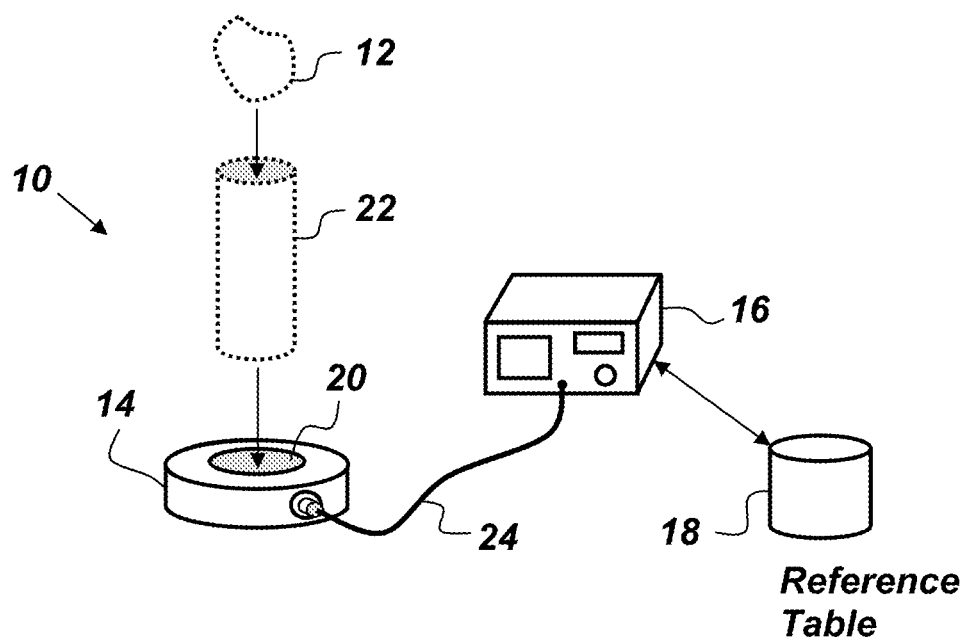
FIG. 1 is an illustration of an apparatus for determining the salinity of a test sample.

FIG. 1 is an illustration of a salinity testing apparatus 10 for determining the salinity of an ionic sample 12. The salinity tester 10 comprises, consists of, or consists essentially of a single current probe 14, a network analyzer 16, and a reference table 18. The current probe 14 comprises a central aperture 20, which is large enough to accommodate a tube 22 that contains the ionic sample 12. The network analyzer 16 is electrically coupled to the current probe 14 with a radio frequency (RF) cable 24. The network analyzer 16 is configured to transmit power into the ionic sample 12 when the tube 22 is positioned within the central aperture 20 and to measure a return loss parameter of a signal voltage waveform reflected from the ionic solution 12. The measured return loss parameter may then be compared to the reference table 18 to determine the level of salinity of the ionic sample 12.

The ionic sample 12 may be any liquid, soil, or sediment. Suitable examples of the ionic sample 12 include, but are not limited to, sea water, urine, brine, and ocean sediment. The sample 12 is held in the tube 22. The tube 22 may be any container capable of holding the sample 12 and fitting within the central aperture 20 of the current probe 14. One example of a suitable embodiment of the tube 22 is a sealed polyethylene container where the salinity tester 10 may be used to determine the salinity of the sample 12 within the tube 22 without breaking the seal or penetrating the sealed tube in any fashion. Another example of a suitable example of the tube 22 is a polyethylene pipe where the sample 12 is a fluid that flows through the pipe. In the pipe embodiment, the salinity tester 10 may be used to determine the salinity of the sample 12 within the tube 22 without any part of the salinity tester 10 coming into physical contact with the sample 12. The tube 22 may be made of metal provided the tube 22 is open on one end. In another embodiment, the tube 22 may be a test tube.

The current probe 14 may be any toroidal current transformer having a single coil and having any desired size and shape. A suitable example of the current probe 14 is the current injection device disclosed in U.S. Pat. No. 6,492,956 to Fischer et al., which is incorporated herein by reference. The current probe 14 may have a solid, ferromagnetic, toroidal core or the core may be split into two or more sections to allow it to be clamped around the tube 22 without cutting into or penetrating the tube 22. The network analyzer 16 may be any vector network analyzer or performance network analyzer. For example, a suitable embodiment of the network analyzer 16 is a model 8753ES, 2-port network analyzer made by Agilent Technologies®.

The reference table 18 may be any look-up table comprising properties of reference samples. For example, the reference table 18 may be a database stored on a computer. The reference table 18 may store measured return loss values from various known reference samples. The reference table 18 may also comprise resonance frequency, bandwidth, and amplitude information pertaining to each measurement of a reference sample. For example, the network analyzer 16 may measure the return loss of each reference sample from 2 MHz to 1600 MHz. The reference table 18 may also comprise reference sample properties from other sources such as industry literature. For example, a reference table 18 of salt concentrations was developed using the following reference samples at multiple known salt concentrations: reverse osmosis water, tap water, drinking water. Each reference sample was measured at each of the following salt concentrations: 0.62, 1.23, 2.46, 9.86, 14.79, 19.72, 24.64, and 29.57 milliliters (0.125, 0.25, 0.5, 2.0, 3.0, 4.0, 5.0, and 6.0 teaspoons) of salt per liter of reference sample.

Figure 2:
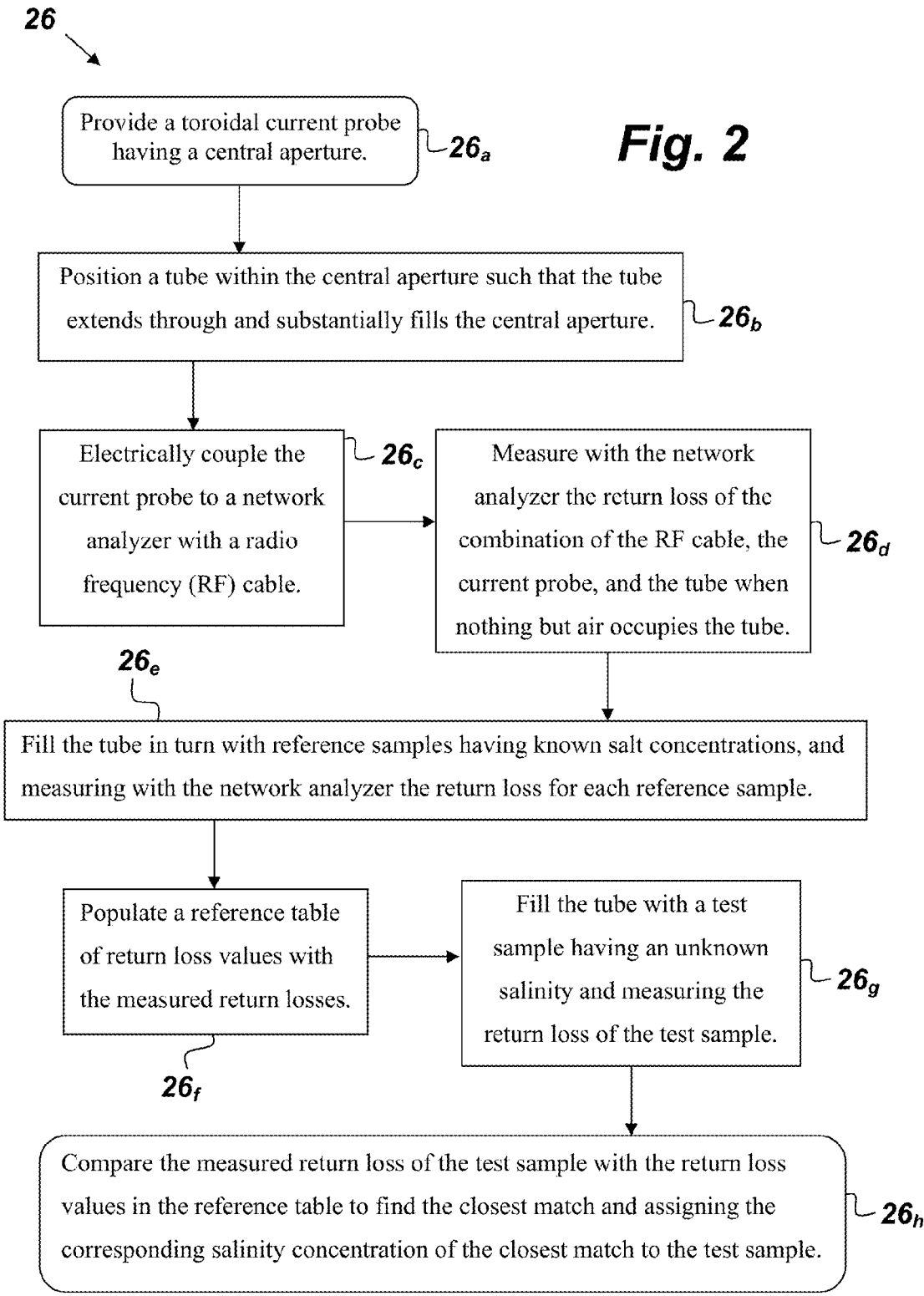
FIG. 2 is a flowchart of a method for determining the salinity of a test sample.

FIG. 2 is a flowchart which depicts one example method 26 of how the salinity tester 10 may be used to determine the salinity of the sample 12. The first step $26_a$ involves providing the current probe 12 having the central aperture 20. The next step $26_b$ provides for positioning the tube 22 within the central aperture 20 such that the tube 22 extends through and substantially fills the central aperture 20. The next step $26_c$ provides for electrically coupling the current probe 14 to the network analyzer 16 with the RF cable 24. The next step $26_d$ provides for measuring with the network analyzer 16 the return loss of the combination of the RF cable 24, the current probe 14, and the tube 22 when nothing but air occupies the tube 22. The next step $26_e$ provides for filling the tube 22 in turn with reference samples having known salt concentrations, and measuring with the network analyzer 16 the return loss for each reference sample. The next step $26_f$ provides for populating the reference table 18 with the measured return losses from steps $26_d$ and $26_e$. The next step $26_g$ provides for filling the tube 22 with the test sample 12 having an unknown salinity and measuring the return loss of the test sample 12. The next step $26_h$ provides for comparing the measured return loss of the test sample 12 with the return loss values in the reference table 18 to find the closest match and assigning the corresponding salinity concentration of the closest match to the test sample 12. The salinity tester 10 may be used to determine the salt content in the sample 12 without immersing the current probe 14 in the sample 12 and without the current probe 14 contacting the sample 12.

The following is a description of an example embodiment of the method described above where the test sample 12 is a urine sample. In this embodiment, the network analyzer 16 was set to perform return loss measurements and the salinity tester 10 was calibrated with a mechanical cal-kit from 2 MHz-1600 MHz by sequentially measuring calibrated open, short, and load terminal modules. Next, the RF cable 24 was connected to the current probe 14. Then the return loss measurement was taken with the network analyzer 16 while the tube 22 was in the central aperture 20 and while the tube 22 was filled with an aqueous solution of 4.93 milliliters (1 teaspoon) of salt dissolved in one liter of drinking water. This last step was repeated for different calibrated plain salt concentrations such as 0.62, 1.23, 2.46, 9.86, 14.79, 19.72 . . . etc. milliliters (0.125, 0.25, 0.5, 2, 3, 4 . . . etc. teaspoons) to develop the reference table 18. Next the urine sample was placed in the tube 22 and the return loss measurement was performed. Then a correlation analysis of the urine sample was performed with the reference table 18 to determine the salt concentration of the urine sample.

Urine comprises dissolved ions of sodium Na+ and chloride Cl−. The Na+ and Cl− ions in a urine sample solution are disassociated and charged respectively. In the urine sample embodiment described above, the tube 22 was a sealed polyethylene container, which was inserted into the central aperture 20 of the current probe 14 and subjected to radio frequency transmission from the network analyzer 16 for return loss measurement. Positively charged ions will respond differently to an alternating electric field than negatively charged ions. The positively charged sodium ions move toward the negatively charged side of the electric field during the negative cycle. Negatively charged chloride ions move toward the positive side of the electric field during the positive cycle. Because these ions are charged and moving in the aqueous solution with the polarity of the alternating electric field set up by the current probe and the network analyzer, they constitute a specific impedance. This specific impedance of the sodium in the urine solution can be derived from the network analyzer scattering parameter measurement.

Reflections of a transmit signal can occur at an impedance mismatch. The ratio of the amplitude of the reflected wave $V_r$ to the amplitude of the incident wave $V_i$ is known as the reflection coefficient Γ. The reflection coefficient Γ is shown below in Equation 1.

$$\Gamma = \frac{V_r}{V_i} \qquad \text{Eq. 1}$$

When the source $Z_S$ and load $Z_L$ impedances are known values, the reflection coefficient Γ may be given by the following equation:

$$\Gamma = \frac{Z_L - Z_S}{Z_L + Z_S} \qquad \text{Eq. 2}$$

In Equation 2, $Z_S$ is the impedance toward the source and $Z_L$ is the impedance toward the load. Return loss is the negative of the magnitude of the reflection coefficient Γ in decibels dB.

Since power is proportional to the square of the voltage, return loss may be given by the following equation:

$$RL \text{ (dB)} = -20 \log_{10} |\Gamma| \quad \text{Eq. 3}$$

According to Equation 3, a good impedance match between the source and the load may be accomplished if the reflected power is small in comparison to the incident power—such as would be indicated by a large, positive return loss value.

When the network analyzer 16 is set to perform return loss measurements, the network analyzer 16 transmits power to the sample 12 via the current probe 14 and measures the reflected power from the sample 12. Return loss measurements may be taken by the network analyzer 16 of many different reference samples, each sample having a unique known concentration of sodium and chloride ions. The reference table 18 may be populated with the resulting return loss measurements. The incident power to the reflected power return loss measurements of the reference samples may be used to obtain corresponding resonance frequency, bandwidth, and amplitude values for each reference sample, which values may also be stored in the reference table 18. The referenced return loss measurement is a good salinity indicator of the total number of sodium ions in the sample 12. Statistical correlation techniques may be used to compare the return loss measurement of the sample 12 with the values in the reference table 18 to find a closest match reference sample. The properties and/or identity of the closest matched reference sample may then be ascribed to the sample 12. This method of using the salinity tester 10 is not limited to sodium chloride in urine analysis, but can also be used for any ionic sample conductivity measurement. For example, potassium K+ in electrolyte solution has different resonance and amplitude than sodium Na+. Accordingly, the salinity tester 10 may also be used to determine the level of potassium in a given sample 12.

Figure 3:
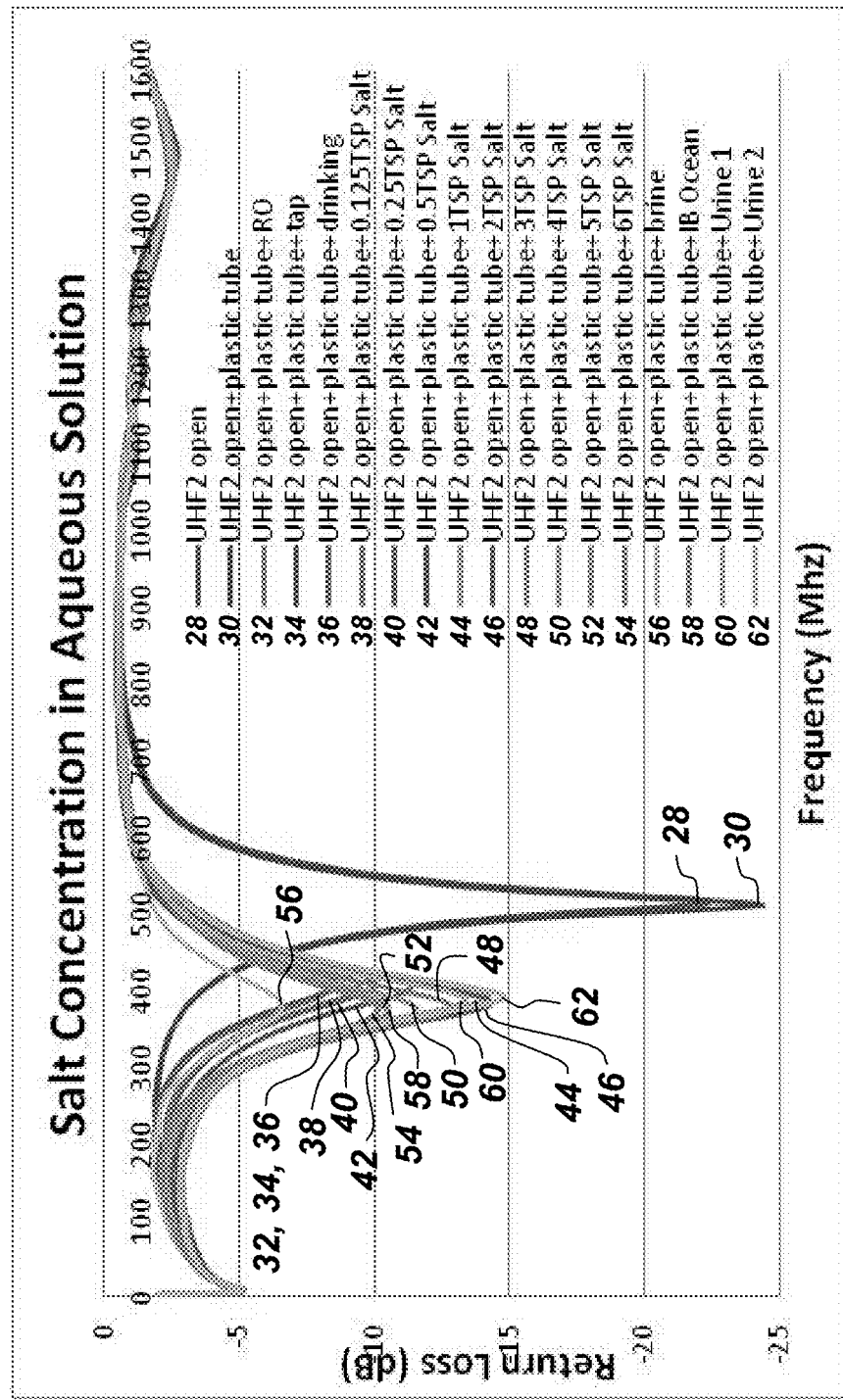
FIG. 3 is a plot of measured return loss values from 2 to 1600 MHz for several conditions of a salinity tester.

FIG. 3 is a plot of measured return loss values from 2 to 1600 MHz for several conditions of the salinity tester 10. A line trace for each condition is shown separately in FIGS. 4A through 12B. For all the conditions measured and depicted in FIGS. 3-12B, the following experimental setup was used. The tube 22 was a polyethylene tube having a length of 14.2875 cm (5.625 inches) and an inner diameter of 2.8575 cm (1.125 inches). The current probe 14 was a UHF2 420-450 MHz current probe manufactured by Fischer Custom Communications, Inc. having an inner diameter of 3.175 cm (1.25 inches), an outer diameter of 9.2075 cm (3.625 inches), and a height of 7.62 (3.0 inches). The network analyzer was a Site Master S312D Cable and Antenna Analyzer from Anritsu®. The network analyzer 16 was connected to the current probe 14 with a 91.44 cm (3 feet) RF cable from Cable X-perts, Inc.

Figure 4A:
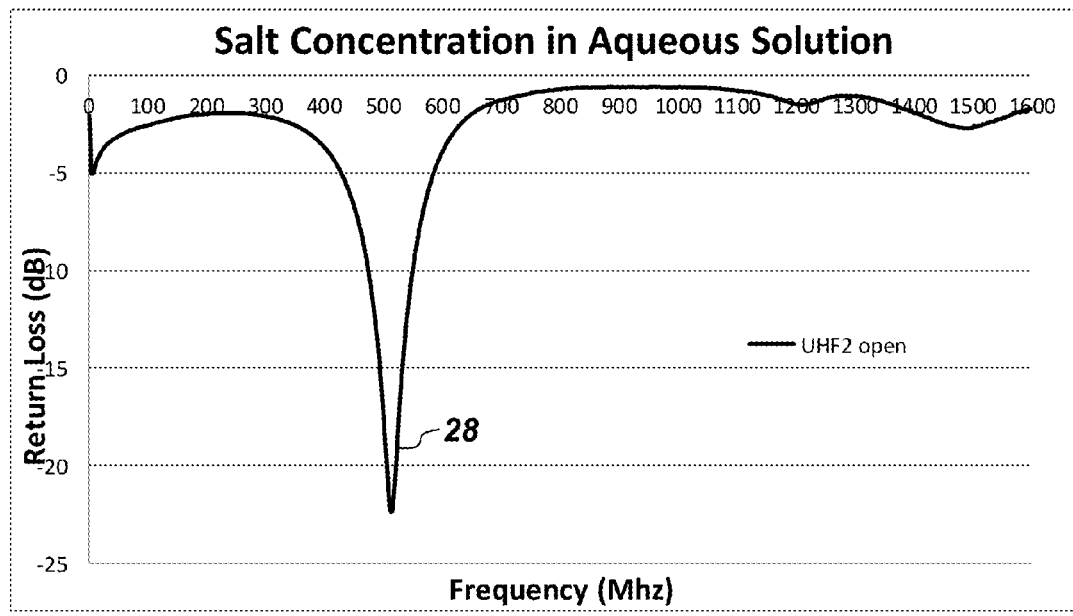
FIGS. 4A through 12B are separate plots of measured return loss values versus frequency for each one of the line traces in FIG. 3.
Figure 4B:
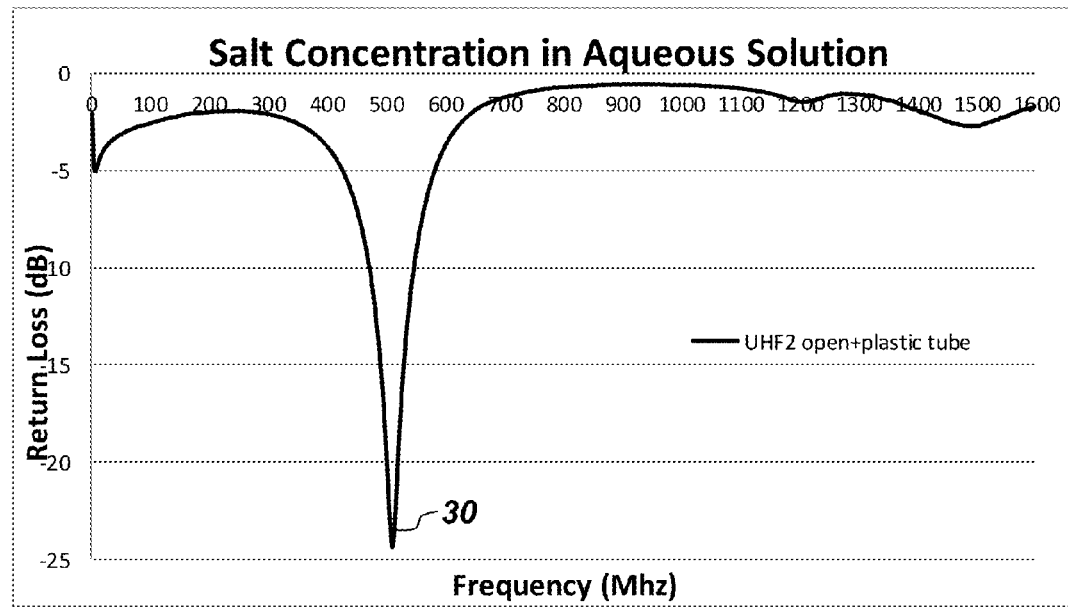
Figure 5A:
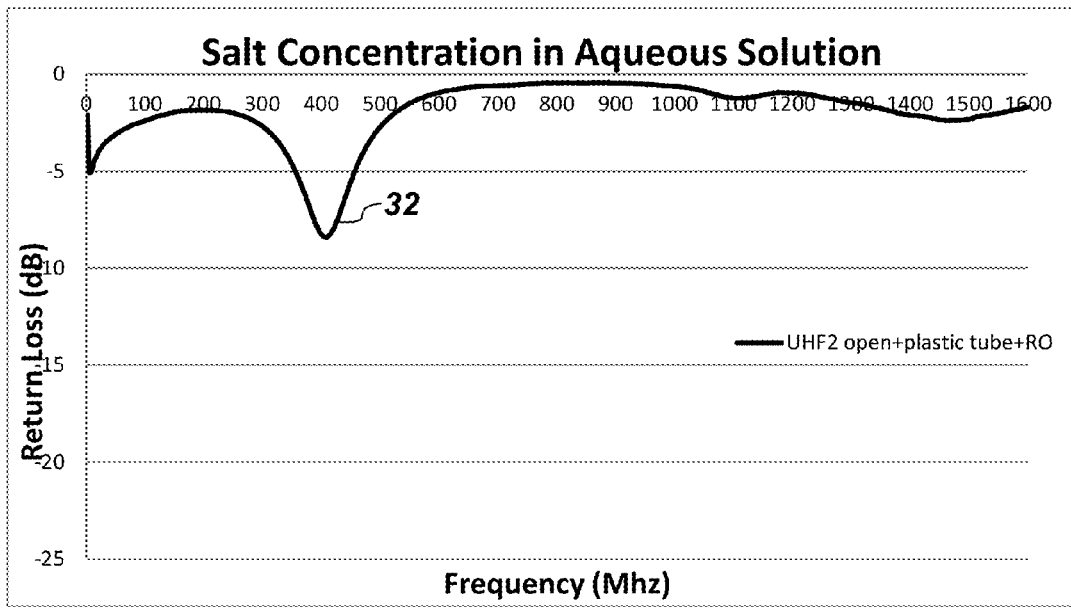
Figure 5B:
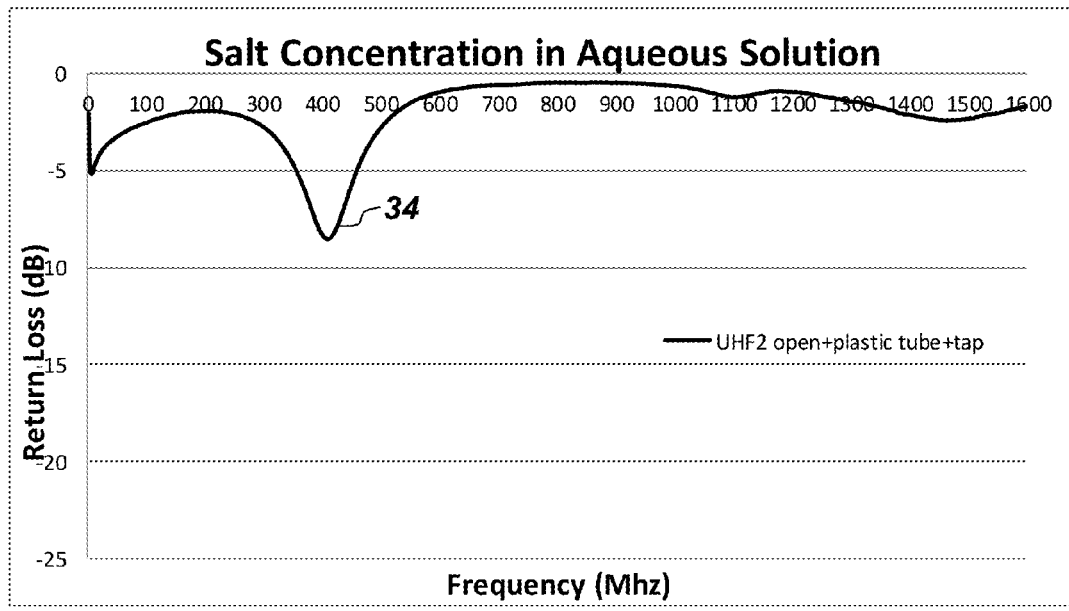
Figure 6A:
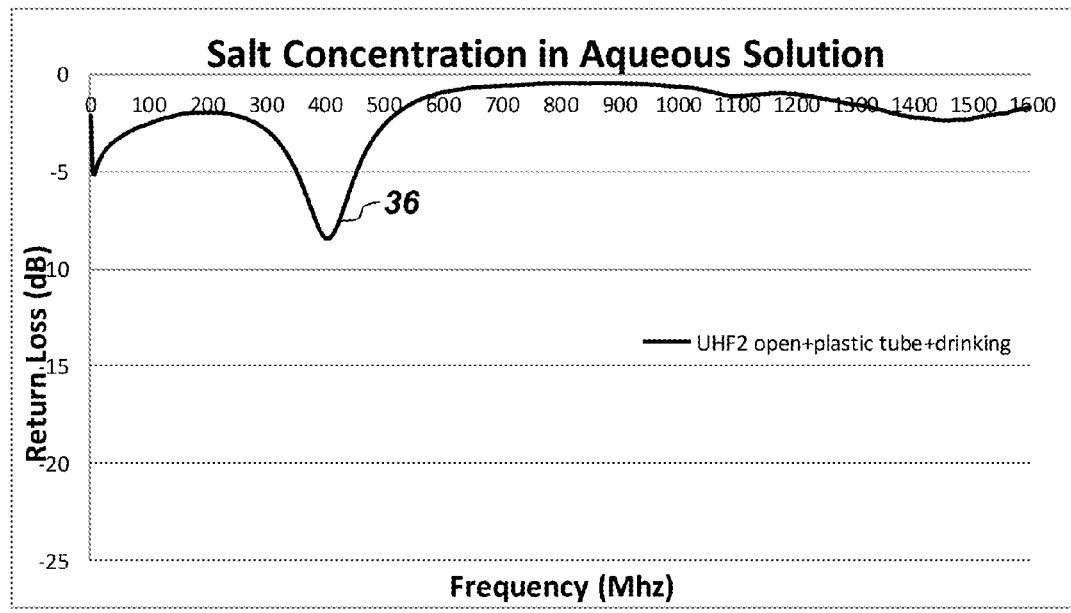
Figure 6B:
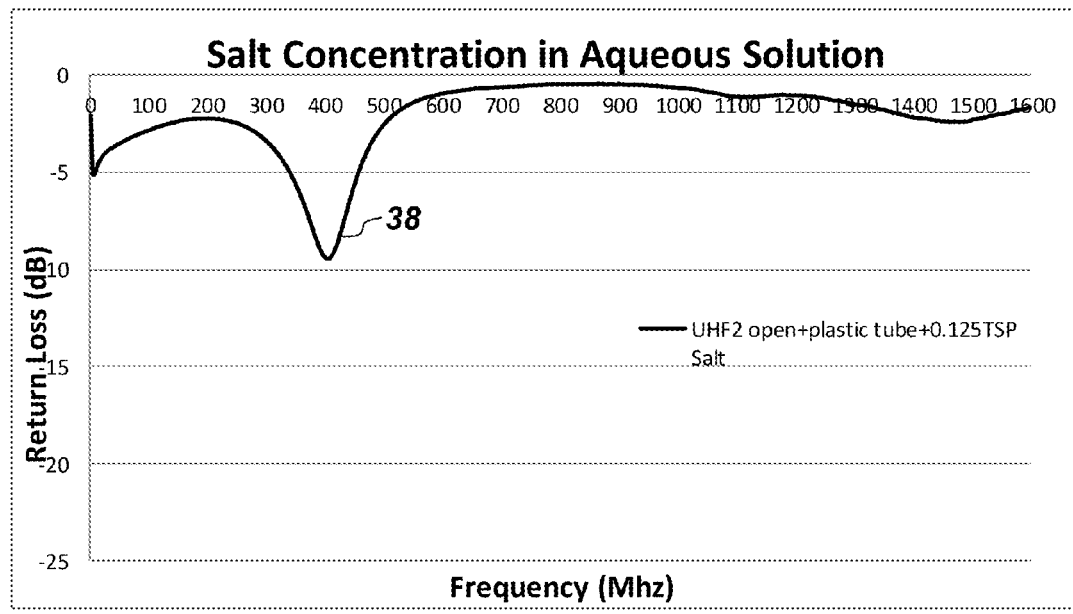
Figure 7A:
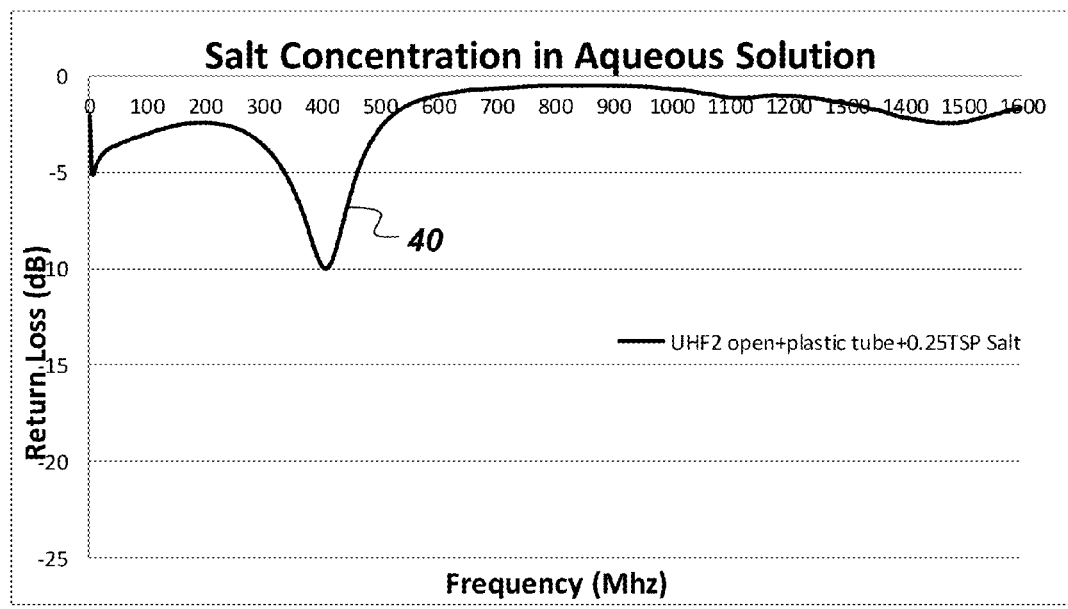
Figure 7B:
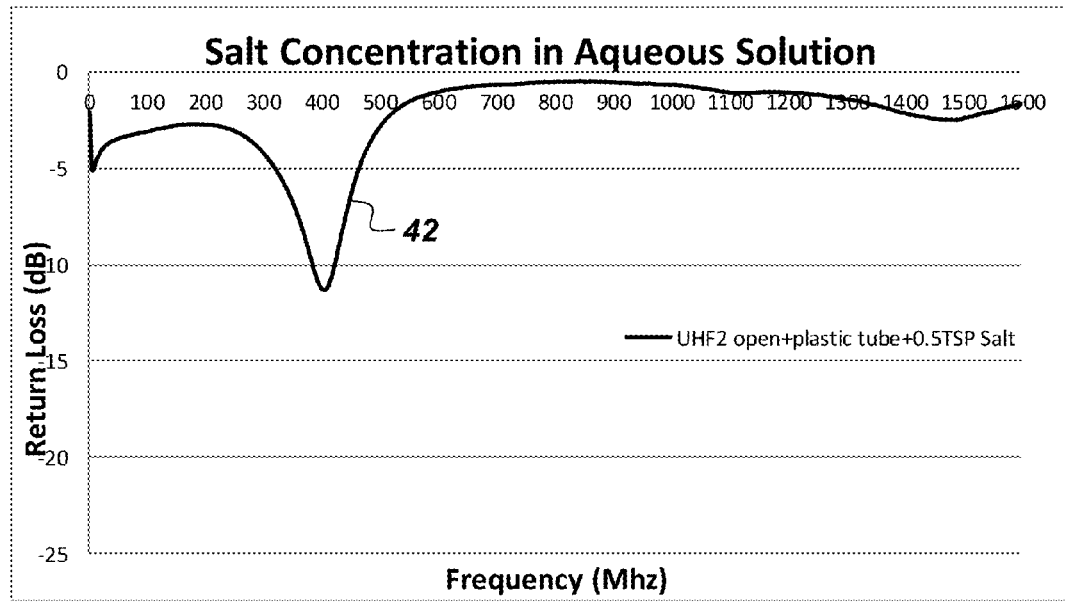
Figure 8A:
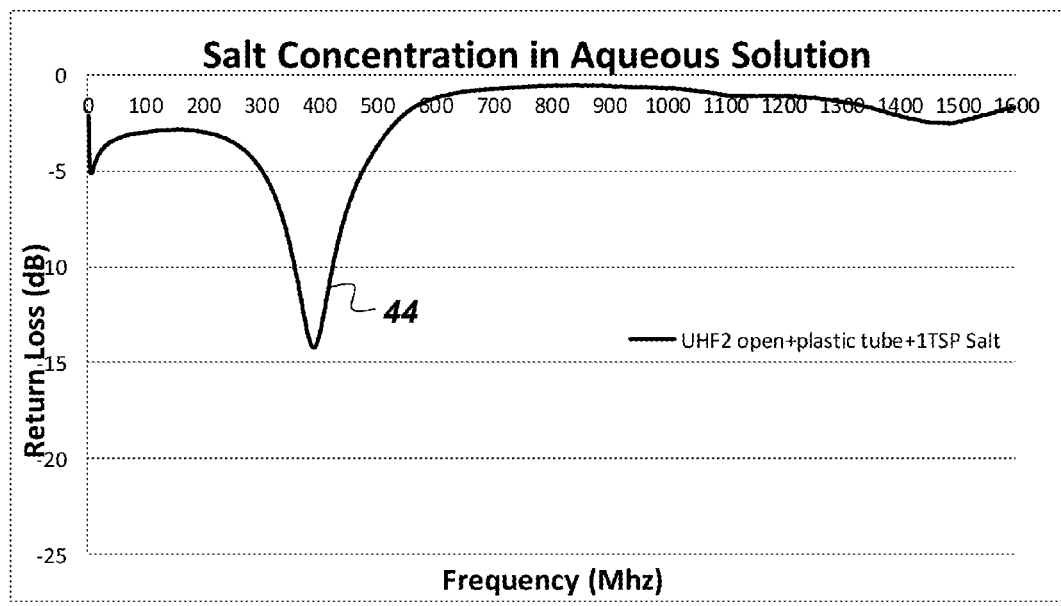
Figure 8B:
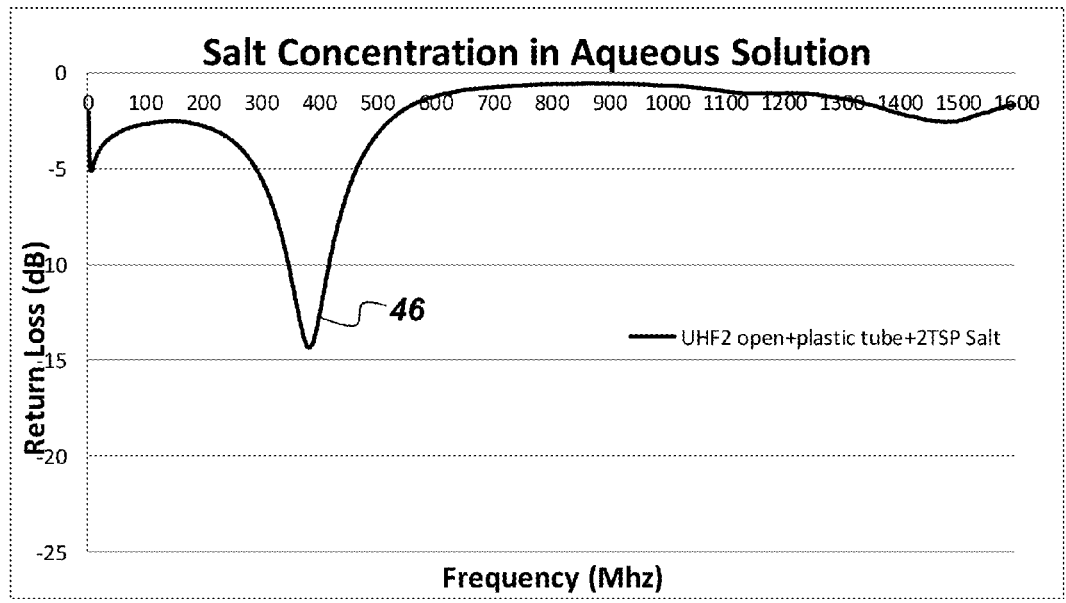
Figure 9A:
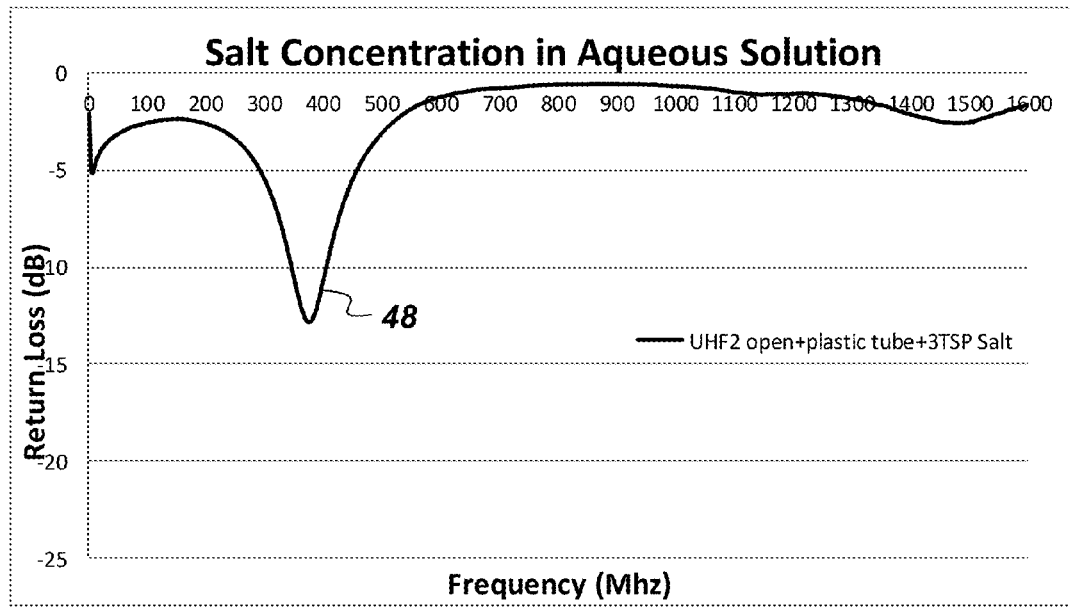
Figure 9B:
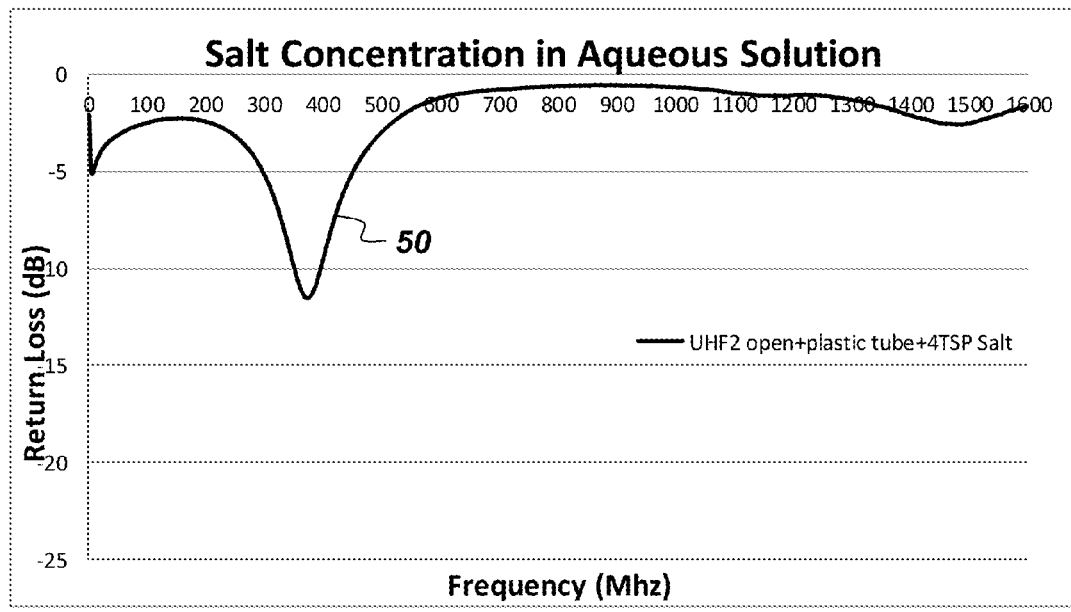
Figure 10A:
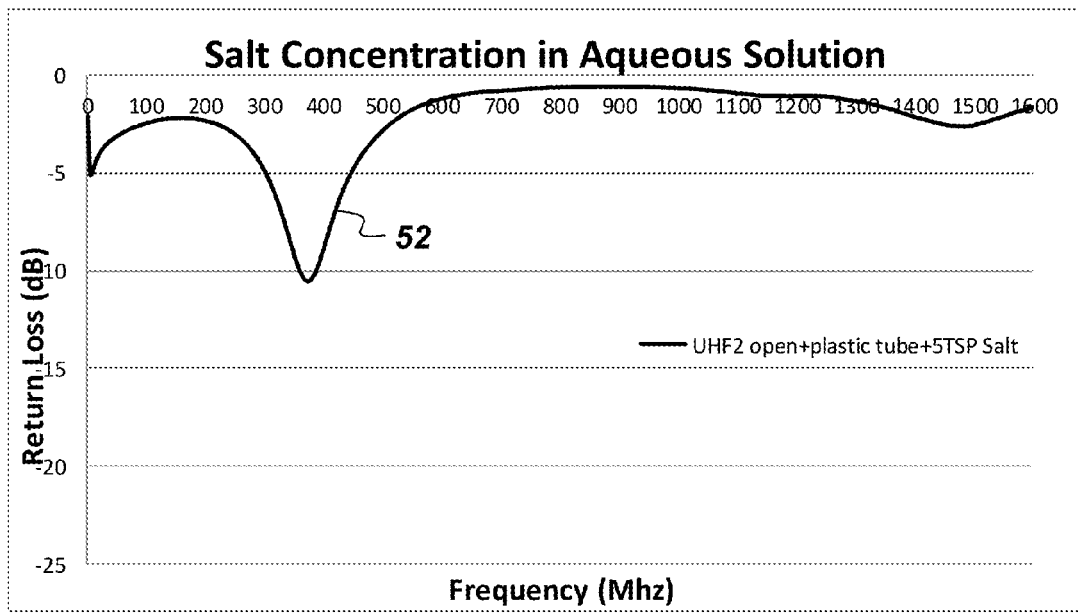
Figure 10B:
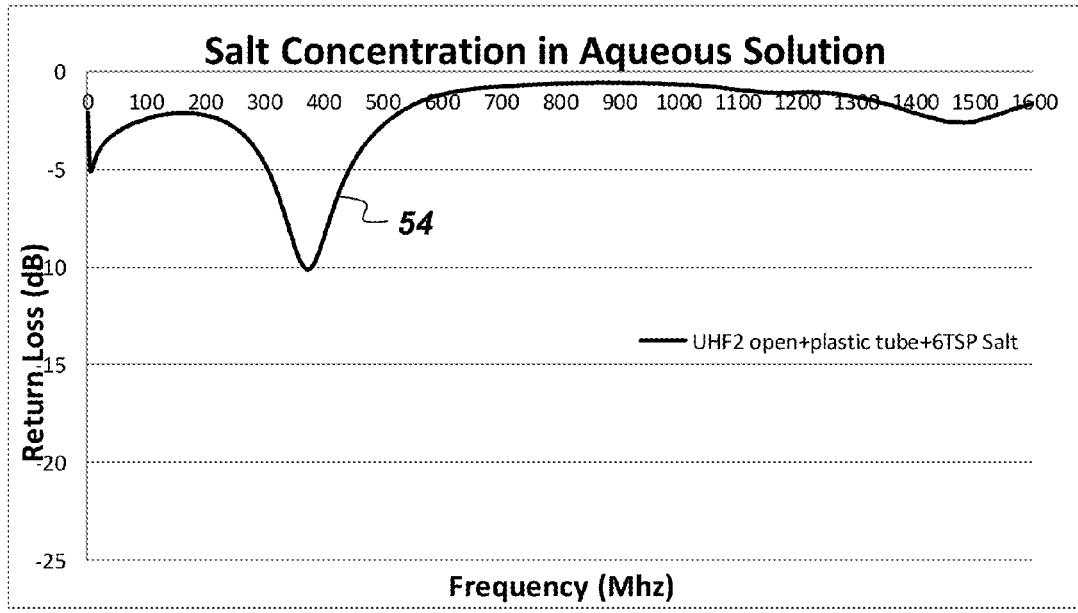
Figure 11A:
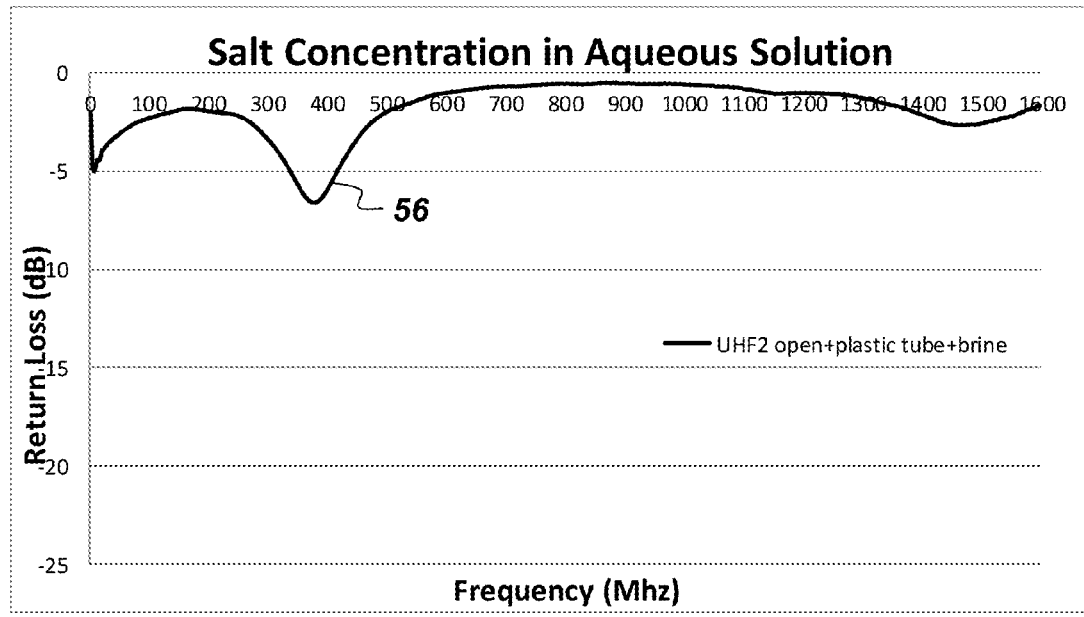
Figure 11B:
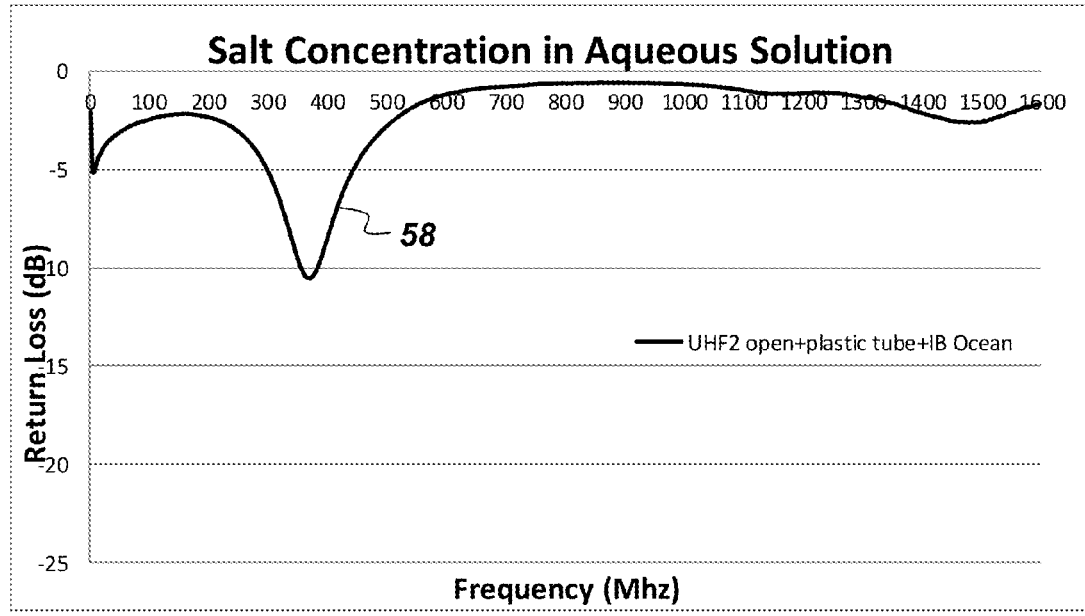
Figure 12A:
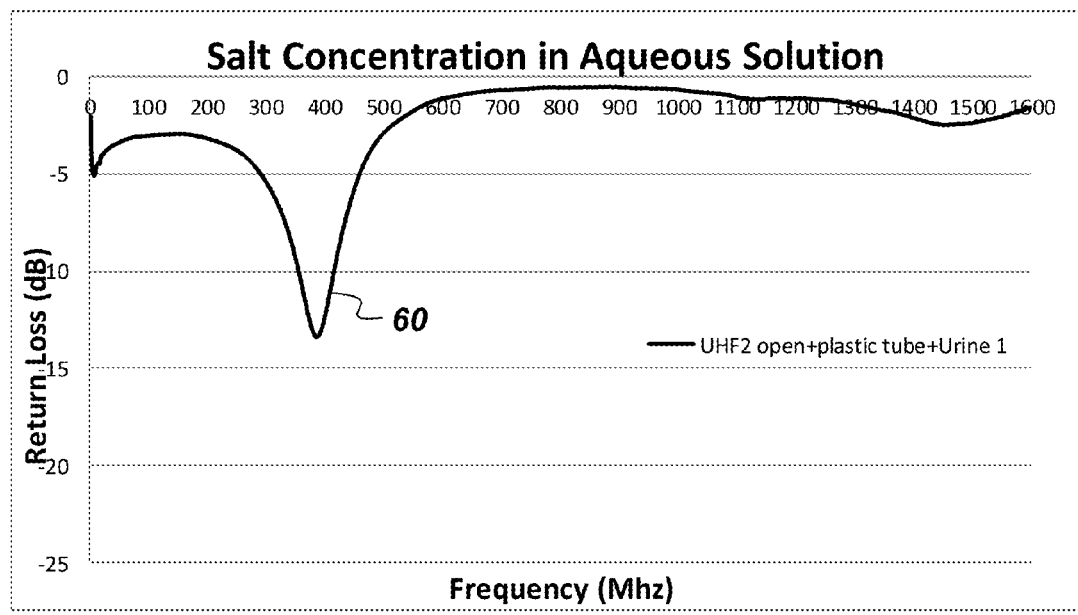
Figure 12B:
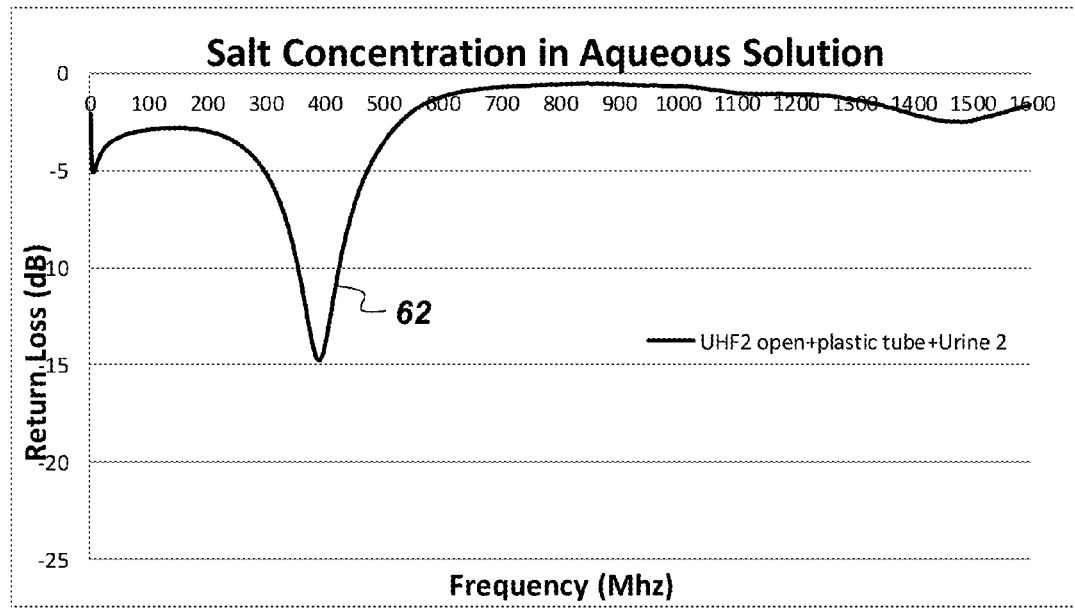

Line trace 28, as shown in FIGS. 3 and 4A, represents the measured return loss of the salinity tester 10 with nothing but air in the central aperture 20 of the current probe 14. Line trace 30, as shown in FIGS. 3 and 4B, represents the measured return loss of the salinity tester 10 with an empty tube 22 positioned in the central aperture 20. Line trace 32, as shown in FIGS. 3 and 5A, represents the measured return loss of the salinity tester 10 with the tube 22—positioned in the central aperture 20—filled with reverse osmosis (RO) water. RO water is more saturated with salts and oxygen than distilled water. Line trace 34, as shown in FIGS. 3 and 5B, represents the measured return loss of the salinity tester 10 with the tube 22 in the central aperture 20 filled with tap water. Line trace 36, as shown in FIGS. 3 and 6A, represents the measured return loss of the salinity tester 10 with the tube 22 in the central aperture 20 filled with filtered, drinking water from a drinking fountain. Line trace 38, as shown in FIGS. 3 and 6B, represents the measured return loss of the salinity tester 10 with the tube 22 in the central aperture 20 filled with the reference solution of drinking water and 0.62 milliliters (0.125 teaspoons) of salt. Line trace 40, as shown in FIGS. 3 and 7A, represents the measured return loss of the salinity tester 10 with the tube 22 in the central aperture 20 filled with the reference solution of drinking water and 1.23 milliliters (0.25 teaspoons) of salt. Line trace 42, as shown in FIGS. 3 and 7B, represents the measured return loss of the salinity tester 10 with the tube 22 in the central aperture 20 filled with the reference solution of drinking water and 2.46 milliliters (0.5 teaspoons) of salt. Line trace 44, as shown in FIGS. 3 and 8A, represents the measured return loss of the salinity tester 10 with the tube 22 in the central aperture 20 filled with the reference solution of drinking water and 4.93 milliliters (1.0 teaspoons) of salt. Line trace 46, as shown in FIGS. 3 and 8B, represents the measured return loss of the salinity tester 10 with the tube 22 in the central aperture 20 filled with the reference solution of drinking water and 9.86 milliliters (2.0 teaspoons) of salt. Line trace 48, as shown in FIGS. 3 and 9A, represents the measured return loss of the salinity tester 10 with the tube 22 in the central aperture 20 filled with the reference solution of drinking water and 14.79 milliliters (3.0 teaspoons) of salt. Line trace 50, as shown in FIGS. 3 and 9B, represents the measured return loss of the salinity tester 10 with the tube 22 in the central aperture 20 filled with the reference solution of drinking water and 19.72 milliliters (4.0 teaspoons) of salt. Line trace 52, as shown in FIGS. 3 and 10A, represents the measured return loss of the salinity tester 10 with the tube 22 in the central aperture 20 filled with the reference solution of drinking water and 24.64 milliliters (5.0 teaspoons) of salt. Line trace 54, as shown in FIGS. 3 and 10B, represents the measured return loss of the salinity tester 10 with the tube 22 in the central aperture 20 filled with the reference solution of drinking water and 29.57 milliliters (6.0 teaspoons) of salt. Line trace 56, as shown in FIGS. 3 and 11A, represents the measured return loss of the salinity tester 10 with the tube 22 in the central aperture 20 filled with a test sample 12 of brine. Line trace 58, as shown in FIGS. 3 and 11B, represents the measured return loss of the salinity tester 10 with the tube 22 in the central aperture 20 filled with a test sample 12 of ocean water from Imperial Beach in San Diego, Calif. Line trace 60, as shown in FIGS. 3 and 12A, represents the measured return loss of the salinity tester 10 with the tube 22 in the central aperture 20 filled with a test sample 12 of urine collected on a first day. Line trace 62, as shown in FIGS. 3 and 12B, represents the measured return loss of the salinity tester 10 with the tube 22 in the central aperture 20 filled with a test sample 12 of urine collected on a second day.

FIG. 13 is a table showing the results of a correlation analysis. A correlation analysis may be performed on the return loss measurement results to determine the sodium level of a given sample 12. For example, Microsoft® Excel's® correlation function was used to analyze the two urine samples from different days and ocean water from San Diego Imperial Beach. The results of that analysis are given in FIG. 5. Several instances of high correlation are circled. The ocean water sample 12 correlated with the reference solutions containing 24.64 to 29.57 milliliters (5-6 teaspoons), which is consistent with known salt concentrations of ocean water. The urine sample 12 from the first day correlated with the reference solution with 9.86 milliliters (2.0 teaspoons) of salt. The urine sample 12 from the second day correlated with the reference solution with 4.93 milliliters (1.0 teaspoons) of salt. The urine sample 12 from the second day also correlated with the urine sample 12 from the first day.

From the above description of the method for using the salinity tester 10, it is manifest that various techniques may be used for implementing the concepts of the method without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the salinity tester 10 is not limited to the particular embodiments described herein, but is capable of many embodiments without departing from the scope of the claims.

I claim:

1. An apparatus for determining the salinity of an ionic sample consisting essentially of:
   a tube configured to contain the ionic sample;
   a single current probe having a central aperture that accommodates the tube that contains the ionic sample;
   a network analyzer electrically coupled to the current probe, wherein the network analyzer is configured to transmit test signal voltage into the ionic sample such that the tube is the only part of the apparatus in physical contact with the ionic sample, and wherein the network analyzer is further configured to measure a return loss parameter of a signal voltage waveform reflected from the ionic sample; and
   a reference table of reference sample properties to which the measured return loss parameter is compared to determine the level of salinity of the ionic sample.

2. The apparatus of claim 1, wherein the current probe is a clamp on current probe that may be clamped around the tube without cutting into or penetrating the tube.

3. The apparatus of claim 2, wherein the tube is a polyethylene pipe.

4. The apparatus of claim 3, wherein the sample is a liquid moving through the polyethylene pipe.

5. The apparatus of claim 1, wherein the tube is a test tube.

6. The apparatus of claim 1, wherein the sample is a liquid.

7. The apparatus of claim 6, wherein the sample is urine.

8. The apparatus of claim 6, wherein the sample is sea water.

9. The apparatus of claim 1, wherein the sample is a soil sample.

10. A method for determining the salinity of a test sample comprising the following steps:
    a. providing a toroidal current probe having a central aperture;
    b. positioning a tube within the central aperture such that the tube extends through and substantially fills the central aperture;
    c. electrically coupling the current probe to a network analyzer with a radio frequency (RF) cable;
    d. measuring with the network analyzer the return loss of the combination of the RF cable, the current probe, and the tube when nothing but air occupies the tube;
    e. filling the tube in turn with reference samples having known salt concentrations, and measuring with the network analyzer the return loss for each reference sample;
    f. populating a reference table of return loss values with the measured return losses from steps (d) and (e);
    g. filling the tube with the test sample having an unknown salinity and measuring the return loss of the test sample; and
    h. comparing the measured return loss of the test sample with the return loss values in the reference table to find the closest match and assigning the corresponding salinity concentration of the closest match to the test sample.

11. The method of claim 10, wherein the step of positioning a tube within the central aperture is accomplished by clamping the current probe around the tube.

12. The method of claim 11, wherein the tube is a polyethylene pipe.

13. The method of claim 12, wherein the test sample is a liquid moving through the pipe.

14. The method of claim 10, wherein the test sample is urine.

15. The method of claim 10, wherein the step of measuring with the network analyzer the return loss of the combination of the RF cable, the current probe, and the tube when nothing but air occupies the tube is performed over a frequency range of 2 MHz-1600 MHz.

16. The method of claim 10, wherein the tube is a sealed container that is never opened during performance of any of the steps a-h.

17. The method of claim 10, wherein the test sample is sea water.

18. The method of claim 10, wherein statistical correlation techniques are used to find the closest match.

19. The method of claim 10, wherein the current probe is never immersed in the test fluid during any of the steps a-h.

20. A method for determining the salinity of a test sample comprising the following steps:
    a. providing a toroidal current probe having a central aperture;
    b. positioning a non-conductive tube within the central aperture such that the tube extends through and substantially fills the central aperture;
    c. electrically coupling the current probe to a network analyzer with a radio frequency (RF) cable;
    d. measuring with the network analyzer the return loss of the combination of the RF cable, the current probe, and the tube when nothing but air occupies the tube to calibrate the network analyzer;
    e. populating a reference table with resonance frequency, bandwidth, and amplitude properties as measured by the network analyzer and the toroidal current probe for a plurality of reference aqueous solutions;
    f. filling the tube with an aqueous solution test sample having an unknown salinity and measuring the return loss of the test sample;
    g. obtaining resonance frequency, bandwidth, and amplitude properties of the test sample based on the measured return loss; and
    h. comparing the properties of the test sample with the properties in the reference table to find the closest match aqueous solution and assigning a corresponding salinity concentration of the closest match aqueous solution to the test sample.

\* \* \* \* \*